United States Patent [19]

Zeiser

[11] 4,371,339
[45] Feb. 1, 1983

[54] DENTURE MOLD, AND METHOD OF AND ARRANGEMENT FOR ITS MANUFACTURE

[76] Inventor: Manfred P. Zeiser, Im Wolfsgalden 8, 7141 Schwieberdingen, Fed. Rep. of Germany

[21] Appl. No.: 213,549

[22] Filed: Dec. 5, 1980

[30] Foreign Application Priority Data

Dec. 11, 1979 [DE] Fed. Rep. of Germany ....... 2949697

[51] Int. Cl.³ .............................................. A61C 19/00
[52] U.S. Cl. ....................................... 433/74; 433/60; 433/53; 433/29
[58] Field of Search ....................... 433/74, 53, 60, 75, 433/29

[56] References Cited

U.S. PATENT DOCUMENTS

| | | | |
|---|---|---|---|
| 317,259 | 5/1885 | Williams | 433/221 |
| 1,130,892 | 3/1915 | Dettinger et al. | 433/211 |
| 1,397,067 | 11/1921 | Williams | 433/221 |
| 2,669,780 | 2/1954 | Mann | 433/74 |
| 2,842,845 | 7/1958 | Carlson | 433/74 |
| 2,911,722 | 11/1959 | Benfield et al. | 433/60 |
| 3,126,632 | 3/1964 | Weissman | 433/60 |
| 3,153,283 | 10/1964 | Weissman | 433/74 |
| 3,255,992 | 6/1966 | Kersten | 433/74 |
| 3,277,576 | 10/1966 | Kraft | 433/74 |
| 3,478,428 | 11/1969 | Stengel | 433/74 |
| 3,498,580 | 3/1970 | Wilson | 433/74 |
| 3,521,354 | 7/1970 | Stern et al. | 433/74 |
| 3,581,398 | 6/1971 | Thomas | 433/74 |
| 3,890,710 | 6/1975 | Jaeger | 433/74 |
| 3,931,677 | 1/1976 | Tinder | 433/74 |
| 3,937,773 | 2/1976 | Huffman | 433/74 |
| 4,021,916 | 5/1977 | Spalten | 433/74 |
| 4,054,995 | 10/1977 | Yoshida | 433/74 |

FOREIGN PATENT DOCUMENTS 2625950 12/1977 Fed. Rep. of Germany ........ 433/74
2653743 6/1978 Fed. Rep. of Germany ........ 433/74

Primary Examiner—Gene Mancene
Assistant Examiner—John J. Wilson
Attorney, Agent, or Firm—Michael J. Striker

[57] ABSTRACT

A denture mold for making teeth prostheses has a base element for releasably supporting a positive copy of teeth and made of a mold material, and a plurality of pins arranged to connect the positive copy with the base element, wherein the base element is formed as a prefabricated plate of a shape-retaining material and the pins are releasably arranged on the plate parallel to one another and fixed on the same, so that the plate serves as a holder for the pins during making of the positive copy, whereupon the plate serves as a base of the denture mold. The denture mold is manufactured by releasably arranging a plurality of pins on the plate in correspondence with a negative denture impression, filling the negative denture impression with a mold material, dipping the pins into the mold material, and hardening the latter to form a positive copy of the teeth. An arrangement for manufacturing the denture mold has a supporting element for placing a denture impression thereon, and a vertically adjustable holding element arranged to hold a plate with a pin and formed as a frame provided with a throughgoing opening which is greater than the denture impression and is arranged so that the plate can be releasably fixed in the opening in at least one predetermined position.

41 Claims, 8 Drawing Figures

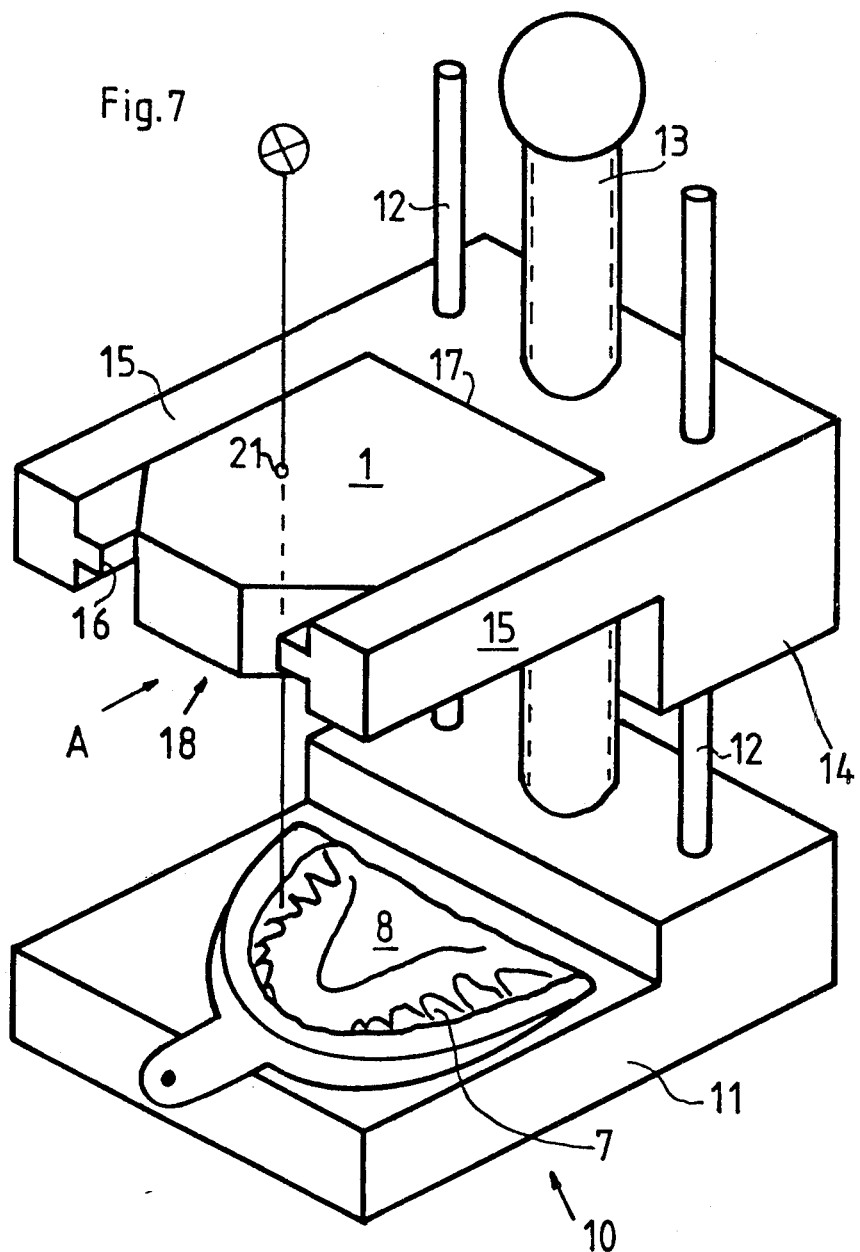

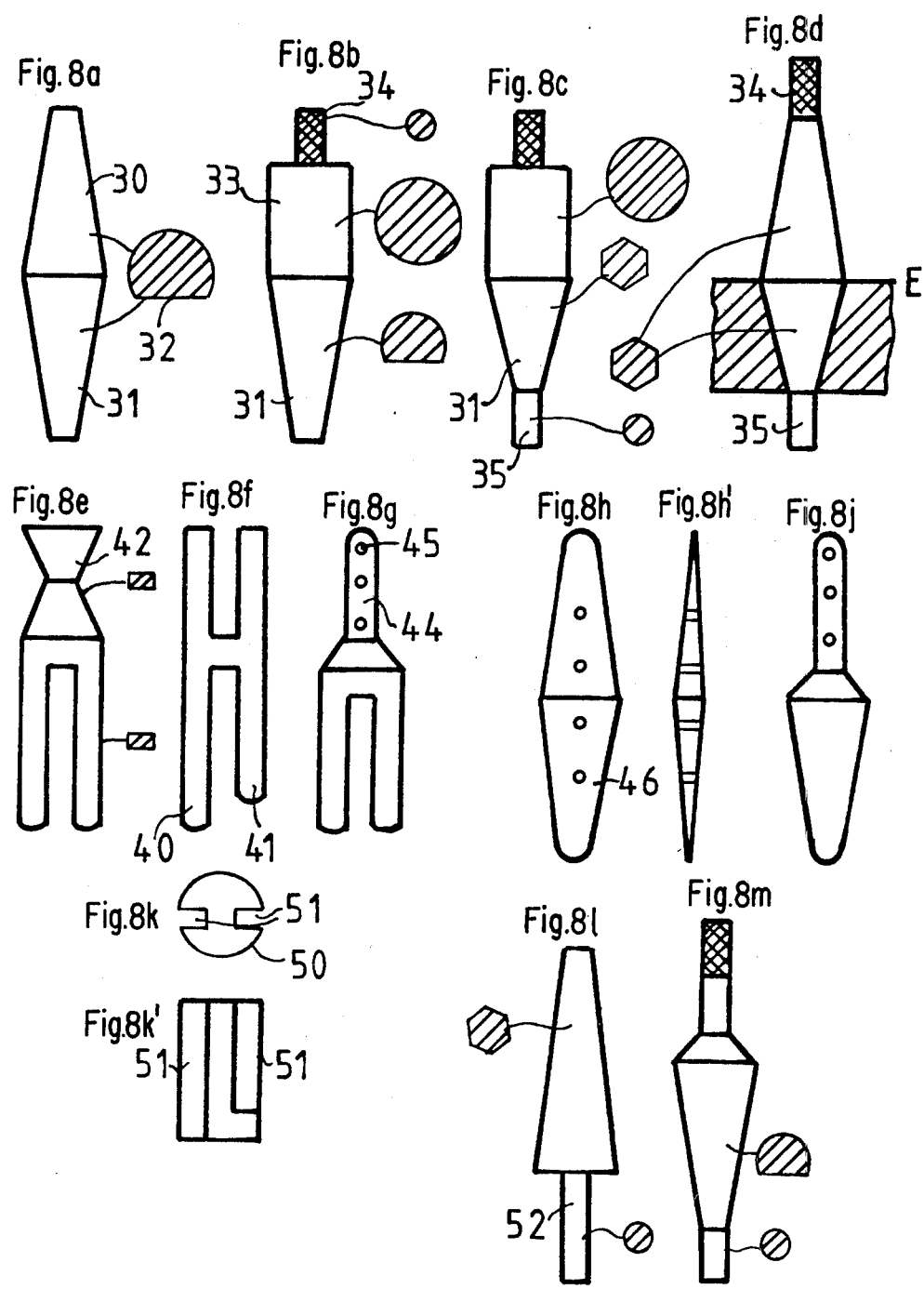

DENTURE MOLD, AND METHOD OF AND ARRANGEMENT FOR ITS MANUFACTURE

BACKGROUND OF THE INVENTION

The present invention relates to a denture mold which is utilized in dental techniques for making teeth prostheses, as well as to a method of and an arrangement for manufacturing such denture molds.

Methods of manufacturing such denture molds are known in the art. In accordance with known methods, pins which are utilized for anchoring a positive copy of several teeth or teeth groups on a base, are arranged with the aid of different auxiliary devices so that they preferably point toward the center of the chewing face of the clinical tooth crowns in the impression. In accordance with the known method, the pins are inserted by their needle-shaped projections directly into the denture impression at the predetermined locations. In accordance with another known method, each pin is fixed on the denture impression with the aid of a holding element formed by a slightly flexible brass wire. Also magnetic holding elements for pins are known wherein the pins are fixed on a curved frame above the denture impression. Finally, it is known to provide an arresting plate which has openings through which holding bars extend, and to mount the pins by short pipe pieces on the holding bars. All the above-mentioned methods utilize auxiliary devices for exact fixing of the pins relative to the denture impression. This has the disadvantage in the fact that despite the provision of special holding elements, the exact arrangement of the pins is not guaranteed. The pins which are not exactly parallel make difficult the subsequent assembling and disassembling of the molds.

After fixing of the pins, the denture impression is filled with mold material, such as for example a special hardening gypsum. After hardening, the holding elements are removed from the pins. The pins are not anchored in the positive denture copy. After this, a gypsum base is formed on the mold face from which the pins extend. After the hardening of the gypsum base, its lower side is surface ground. After this, the individual teeth can be separated with the aid of a gypsum saw and later removed from the base for further working. This method is very difficult and time-consuming, inasmuch as it is necessary to wait for hardening of the gypsum base. Especially disadvantageous is the fact that, when the base is constituted of gypsum or other similar materials, volume variations because of hardening expansion take place and the mold does not exactly correspond to the original. The above-mentioned hardening expansion also causes expansion of the pin-receiving openings in the base, and exact location of the pins is no longer guaranteed. The exact location of the pins deteriorates during repeated disassembling of the mold, since during assembling the pin-receiving openings in the gypsum base are rubbed. As a result of these disadvantages, the teeth prostheses made with the aid of such molds must further be worked again with considerable time expenditures.

A further method of manufacturing a denture mold is disclosed in the German Offenlegungsschrift No. 2,455,144. In accordance with this method, first the denture model is manufactured, faced at its lower side, and then placed onto a flate plate. Then from the lower side a plurality of openings are produced in the plate and the pins are anchored in these openings. It is not disclosed how the pins are anchored in the teeth. During drilling of the openings in the plate, simultaneously openings in the teeth are drilled. This method has the disadvantage that during drilling in a gypsum mold, material particles can burst through and thereby an exact guidance of the pins in the denture mold is not guaranteed. Moreover, the facing of the hardened gypsum mold is difficult and time-consuming. Finally, still a further method of manufacturing denture molds is known in accordance with which the pins are anchored in the mold during hardening of the mold material. This method is disclosed in the German Offenlegungsschrift No. 2,653,743. However, in accordance with this method the plate serves only as an auxiliary tool for respective fixing the pins, and does not serve as a base for the final mold.

SUMMARY OF THE INVENTION

Accordingly, it is an object of the present invention to provide a denture mold as well as a method of and an arrangement for manufacturing the same, which avoids the disadvantages of the prior art.

More particularly, it is an object of the present invention to provide a denture mold, as well as a method of manufacturing and an arrangement for manufacturing the same, which guarantee fast and simple manufacture of the denture mold with high accuracy.

In keeping with these objects and with others which will become apparent hereinafter, one feature of the present invention resides in a denture mold which has a base element for releasably supporting a positive copy of teeth, made of a mold material, and a plurality of pins arranged to connect the positive copy with the base element, wherein the base element is formed as a prefabricated plate of a shape-retaining material and the pins are releasably arranged on the plate parallel to one another and fixed on the same, so that the plate serves as a holder for the pins during making of the positive copy, whereupon the plate serves as a base of the denture mold.

When the denture mold is designed in accordance with the present invention, exact arrangement of the pins is guaranteed, since the pins are directly anchored in the base element formed as a plate of shape-retaining material. After the hardening of the positive copy of teeth, the base element serves as a base for the denture mold. It is not necessary to utilize additional auxiliary elements. Difficult arrangement of the pins is no longer needed. Immediately after the hardening of the mold material in the impression, separation of the teeth can start. So-called trimming of the base is not needed. Volume variations of the base do not take place, and the teeth can be removed from the base plate as often as possible without expanding the pin-receiving openings in the base.

Different materials can be utilized for the plate. The material influences the manner of fixing the pins in the plate. Pressing the pins directly into the plate without additional means or preliminarily heating the pins depend upon the material of the plate. It is especially advantageous when guiding openings are first produced in the plate and the pins are pressed into the openings in heated state. When a thermoplastic synthetic material is utilized for the plate, the walls of the openings are plasticized and assume the outer shape of the pins so that very good correspondence between the pins and the pin openings takes place.

Conventional pins can be utilized in the inventive denture mold. However, it is also possible to provide pins of special construction. It is especially advantageous when the pin has two portions, as considered in longitudinal direction, which portions have different cross-sections and a greater cross-section in the plane of separation which coincides with the contact plane between the base and the mold material. The pin has a very simple construction and is not expensive when it includes two conical portions and is formed as a punched or stamped member. Such pins can also be utilized in known molds.

Another feature of the present invention is a method of manufacturing the above-described denture mold. In accordance with this method, the pins are arranged on the plate of a shape-retaining material so as to extend parallel to one another from the plate, the negative denture impression is filled with a mold material, and the pins are dipped into the mold material and the latter is hardened to form a positive copy of the teeth, wherein during the hardening the plate serves as a holder for all pins, whereas after the hardening the plate serves as a base of the denture mold.

When the method is performed in accordance with the present invention, it is no longer necessary to provide a separate protracted hardening of the base. Fixation of the pins in the base in accordance with predetermined fixing points is less time-consuming than in the known methods, the means utilized for performing this method is simpler and less expensive.

Finally, a further feature of the present invention is an arrangement for manufacturing the above-described denture mold, the arrangement including a supporting element for placing a denture impression thereon, and a vertically adjustable holding element arranged to hold a plate with pins and formed as a frame, wherein the frame has a throughgoing opening which is greater than the denture impression and is arranged so that the plate can be releasably fixed in the opening in at least one predetermined position. When the arrangement is designed in accordance with the present invention, the plate and the denture impression can be repeatedly brought into corresponding positions relative to one another, and fixing points for pins on the plate can be individually determined with high accuracy.

The novel features of the present invention which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 7 is a perspective view of an arrangement for manufacturing the denture mold in accordance with the present invention; and FIG. 8(a-m) are views showing different shapes of the pins.

DESCRIPTION OF THE PREFERRED EMBODIMENTS

Figure 1:
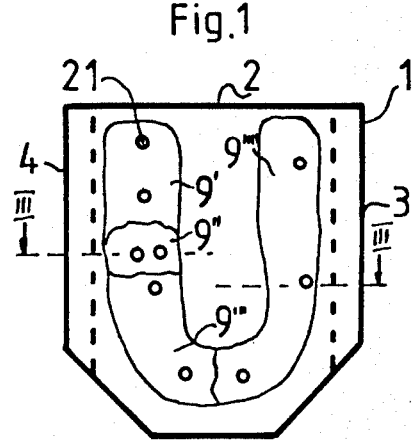
FIG. 1 is a view showing a base plate of a denture mold of a lower jaw, in accordance with the present invention.
Figure 2:
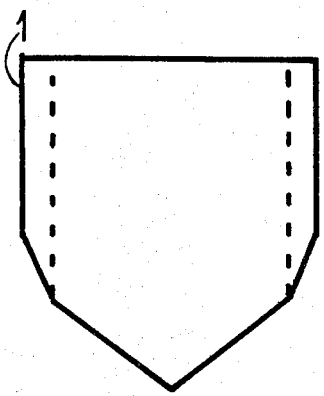
FIG. 2 is a view showing a base plate for a denture mold of an upper jaw.
Figure 3:
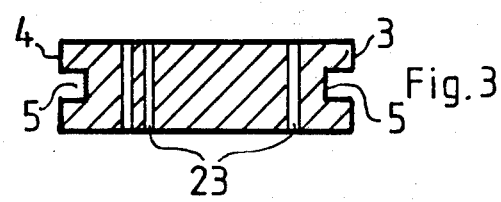
FIG. 3 is a view showing a section of the plate shown in FIG. 1.

FIG. 1 shows the contour of a plate 1 which is utilized for manufacturing a mold or model of a lower jaw. The plate 1 has a polygonal contour which substantially corresponds to the contour of a lower jaw. The lateral edges of the plate 1 extend substantially parallel to the tangents of the outer surfaces of the left molar teeth, eye teeth, and front teeth. FIG. 2 shows a plate for the mold or model of an upper jaw. It is to be understood that the plate 1 may have different shapes, particularly when the mold must represent only a portion of a jaw.

The plate 1 has two guiding surfaces 3 and 4 which extend parallel to one another and are provided with guiding grooves 5. The plate 1 also has an abutment surface 2 extending normal to the guiding surfaces 3 and 4. The guiding surfaces and the abutment surface guarantee that the plate 1 can be repeatedly received into an orientation device to be located in the identical position.

The plate 1 has a thickness of substantially 10 mm. It is constituted of a shape-retaining material. Advantageously, acrylic glass is utilized as the material of the plate, since it is light and at the same time hard and resistant to breakage, and also is easy to be worked. The plate 1 can be constituted of a pellucid material which makes easier the determination of fixing points for pins. However, other thermoplastic synthetic materials may also be utilized, particularly synthetic materials with a low melting points. Metallic materials may also be utilized, such as for example soft aluminum. The properties of the material of the plate depend upon the manner in which the pins are fixed in the plate.

Before discussing FIGS. 3-6, it is advisable to describe an orienting arrangement for manufacturing the denture mold which is shown in FIG. 7 and identified in toto by reference numeral 10. The arrangement has a supporting plate 11 for an impression-receiving member 7 in which a denture impression 8 is located. A holder 14 is vertically movable on guiding rods 12 and a threaded spindle 13. The holder 14 has two arms 15 which extend parallel to one another and are provided with guiding projections 16. The arms 15 are connected with one another by a normally extending abutment web 17 and together with the latter form a frame 18 for the plate 1. The plate 1 can be inserted into the frame 18 by movement in direction of the arrow A. The guiding faces 3 and 4 of the plate 1 slide over the arms 15, and the abutment face 2 of the plate 1 abuts against the abutment web 17. The guiding grooves 5 of the plate 1 cooperate with the guiding projections 16 of the arms 15. It is to be understood that the projections may be formed on the plate 1, whereas the grooves may be formed in the arm 15.

When the plate 1 is received in the frame 18, it is fixed both in horizontal direction and in vertical direction. Thereby, the plate is unmistakably arranged in the frame and exactly fixed relative to the denture impression located under the plate. This initial position is exactly reproducible every time the plate is introduced into the frame 18.

The frame 18 shown in FIG. 7 has one open side. However, the frame may be completely closed at all sides, so that the opening in the plate is peripherally complete or closed. This opening has a contour exactly corresponding to the contour of the plate 1. Thereby, the plate abuts against the frame in all directions in the horizontal plane and can be removed from the frame only in vertical direction. It is important that the opening in the frame 18 be greater or at least equal to the contour of the denture impression.

A method of manufacturing the denture mold is performed in the following manner. First of all, the denture impression 8 is manufactured in a known manner and placed into the impression-receiving element 7. The impression-receiving element 7 is mounted on an occlusion-orienting sheet with the aid of a kneading mass so that not only the occlusion plane extends parallel to the orienting plate, but also the palate edge in the impression extends in correspondence with the central line of the orienting plane or its marking. This operation is known in the art and does not have to be explained in detail. In order to make simpler the showing in FIG. 7, the above-mentioned orientation is performed directly on the supporting plate 10 and the orientation sheet is not utilized. Moreover, means for clamping the impression-receiving element in a predetermined and reproducible position is also not shown in FIG. 7.

After the insertion of the base plate 1 into the frame 18, fixing points 21 for pins 22 are determined. When the plate is constituted of a transparent material, the fixing points can be determined with the aid of a narrowly concentrated light beam extending through the plate 1, as schematically shown in FIG. 7. The light source is so oriented that the light beam falls onto the center of the chewing face of the clinical crown in the impression. Since the denture impression 7 and the base plate 1 are fixed in the arrangement in a corresponding position, the fixing point 21 can be marked on the plate by suitable means very easily, at the locations where the light beam meets the plate.

The fixing points may also be determined by a marking arrangement. A marker of the marking arrangement is first oriented toward the desired point in the impression after removal of the plate, and thereafter the plate is again brought into the corresponding position and the marker is brought into contact with the outer surface of the plate. Naturally, the position of the marking arrangement relative to the orienting arrangement must not be changed. A drilling machine mounted in a standard can be utilized, for example, as the marking arrangement, in which case the drill serves as the marker. The base plate can be simultaneously drilled at the location of the fixing points.

Vertically adjustable heated needles or soldering bits can also be utilized as markers. They are pressed into the plate of a synthetic plastic material in the respective points. The marking arrangements of other constructions may also be utilized. It is important that the predetermined points in the negative denture impression are transferred to the base plate with the scale 1:1.

When all fixing points are provided on the base plate, the pins 22 can be fixed in the latter. FIG. 1 shows the pins 22 and their distribution on the base plate when denture parts 9'–9'''' must be releasably mounted on the base plate, separately from one another.

In accordance with another solution, openings 23 are first produced in the plate 1. A drill with a diameter of 2 or 2.5 mm is suitable for this purpose.

Figure 4:
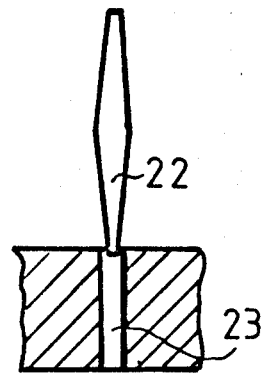
FIG. 4 is an enlarged sectioned fragment of the plate before fixing a pin therein.
Figure 5:
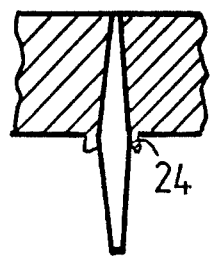
FIG. 5 is a view corresponding to that of FIG. 4 but showing the plate with the pin fixed therein.

As shown in FIG. 4, the diameter of the opening is greater than the diameter of the tip of the pin but smaller than the greatest diameter of the pin portion which is dipped into the plate. After this, the pin 22 in heated state is pressed into the opening 23. The material of the opening wall is momentarily plasticized, and the opening assumes the contour which exactly corresponds to the shape of the pin. This provides for especially accurate fitting between the opening or pin-receiving formation in the base plate and the pin.

When the plate is constituted of a soft metal, the heating of the pin can be dispensed with, and the pin can be inserted into the plate under the action of pressure. The pin produces by cold deformation its own receiving opening. When the plate is constituted of a material with a low melting point, in certain conditions the openings can also be dispensed with. The pin can be heated and directly pressed into the plate in predetermined fixing points. The plate can also be provided with conical openings formed by laser beams, which makes easier the subsequent insertion of the pins into the openings.

An advantageous solution also includes drilling of the openings in the plate and subsequent expansion of the openings with local heating of the plate. Then, the pin can be inserted into the opening in cold state, and the opening wall will thereafter momentarily plasticize. The above-mentioned needle may have the shape of the pin or at least a substantially corresponding shape. In the latter case the subsequent insertion of the pin is easier without jeopardizing the exact fitting of the pin in the opening.

Finally, the pins can be anchored in the plate without pressure and heat, for example by ribbing or spreading. The pins may also be anchored in a sleeve which is screwed in the plate. Moreover, the pins can be glued in blind holes provided in the plate. A safety ring or other arresting means can be utilized for fixing the pins in the plate.

It is important that in each case the pins extend parallel to one another and normal to the plate. This is guaranteed by the openings which are drilled with high accuracy and serve as guides for insertion of the pins. Special holding means for pins can make this process easier. When the opening walls are plastically deformed, very often a bead is formed which forms an extension of the guides for the pin as shown in FIG. 4.

The above-described methods of fixing of the pins in the plate provide for releasable or non-releasable anchoring of the pins in the plate. In correspondence with this, the pins may have different constructions which will be described hereinbelow. After the fixation of the pins, the plate is brought into the predetermined position in the holding frame. The pins extend from the plate in the direction toward the impression. It is now necessary to determine at which height above the occlusion plane the plate must be arranged. In the case of an upper jaw impression, it depends upon whether the palate must be shown or not. Exact orientation is performed by vertical adjustment of the frame 18 with the aid of the threaded spindle 13. It is advantageous always to hold the distance between the plate 1 and the impression 8 as small as possible.

Figure 6:
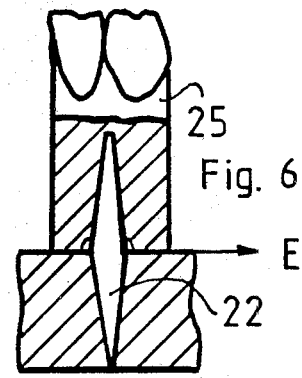
FIG. 6 is a view showing a double teeth piece mounted on the plate.

After this, the impression 8 is filled with a mold material in known manner. The mold material can be also additionally applied to the base plate 1, and this material does not have the same properties. After lowering of the plate, the pins dip into the mold material, and the respective points are located exactly one over the other. After hardening of the mold material which deforms in exact correspondence with the impression and forms a positive copy of the teeth, the positive copy can be removed from the base plate 1. FIG. 6 shows a section of such a denture mold in which the double teeth piece 25 is connected with the plate 1 by the pin 22.

FIG. 8 shows pins having different constructions. The pin of FIG. 8a has two cone-shaped portions 30 and 32 with base faces superimposed over one another. The pin has a substantially circular cross-section which is interrupted only by a flat face identified by reference numeral 32. The face 32 serves as a guiding face and prevents rotation of the pin.

The pin of FIG. 8b has the conical portion 31 connected with a cylindrical portion 33. The latter is provided with a cylindrical projection 34 which has retention means such as knurls or corrugations. The conical portion 31 also has a circular cross-section interrupted by a flat face, whereas the portion 33 has a completely circular cross-section.

The pin of FIG. 8c has a cylindrical projection 35 arranged at the tip of the conical portion 31. The cylindrical projection 35 makes easier the insertion of the pin into the opening. The conical portion 31 may have a polygonal cross-section. This is also true for the pin shown in FIG. 8d which is formed as a double cone with two projections 34 and 35 which can also be knurled.

In all the above-mentioned constructions, the pin has two portions of different cross-section, wherein the cross-section of the pin in a separation plane E is the greatest. The separation plane E advantageously coincides with the contact plane between the plate and the mold material. This is clearly shown in FIGS. 6 and 8d. Contrary to the known constructions in which the pin is also conically increases in the mold material, the inventive constructions eliminate breakage of the opening walls.

As can be seen from FIG. 1, two pins are required for fixing an individual tooth. The orientation of the pins is performed in accordance with the inventive method without difficulties even when the pins are located very close to one another. It is advisable to utilize in this case the pin shown in FIG. 8e, which has two guiding arms 40 and 41. A portion 42 which is inserted into the mold material has a dove-tail shape. The pin of FIG. 8f has an H-shaped cross-section, and its legs may have different lengths. FIG. 8g shows a further modification of the pin of FIG. 8e, in which instead of the dove-tail shaped portion 42, a plurality of through openings 45 are provided in an upper bead portion 44 which runs into the mold material. FIG. 8h shows a front view and FIG. 8h' shows a side view of a further spindle-shaped pin. The through openings are provided in a lower portion 46 and the plasticized material of the plate engages in the through openings. Finally, FIG. 8j shows a spade-shaped pin. All the pins described above can be easily manufactured as punched or stamped parts.

Even though two-arm constructions can be both fixed in the plate and anchored in the mold material without auxiliary means, it is preferable to utilize an anchoring sleeve shown in FIGS. 8k and 8k'. The sleeve 50 has two grooves 51 corresponding to the cross-section of the pin, wherein the length of the grooves is determined in accordance with the length of the arms 40 and 41. The sleeve can be outwardly corrugated or provided with longitudinal indentations and is directly pressed into the opening of the plate. Heating can be dispensed with when the material of the plate has the required resilience and deformability.

FIG. 8l shows a pin with a smooth cylindrical cross-section 52 which is inserted into the opening and glued therein. The pin shown in FIG. 8m substantially corresponds to that of FIG. 8d, but the cylindrical projection of the pin of FIG. 8m has two sections of which only one is corrugated.

It should be mentioned that at least some pins shown in FIG. 8 can be utilized together with the known methods, and thereby the pins per se are characterized by the inventive features. It should be mentioned again that at least some pins having the projections which dip into the mold material can be anchored in the plate, particularly when it is desired to provide a releasable connection between the pin and the mold and a non-releasable connection between the pin and the plate.

A particularly simple and time-saving method of fixing of the pins in the plate includes simultaneous insertion of all pins in one operational step. All pins may be inserted into the openings of the plate without application of force. The pins dip only insignificantly into the openings having the diameter selected in correspondence with the conical cross-section of the pins (see FIG. 4). The plate with loosely inserted pins is then subjected to thermal treatment in hot circulating air at temperatures about 200° C. Thereby, the material of the plate and each pin are simultaneously and effectively heated up so that the plate material in the region of the openings yields without distorting of the entire plate. After this, all pins are pressed into the openings by a common pressure-transmitting plate member which abuts against the free ends of the pins and the opening walls are deformed in correspondence with the cross-section of the pins. After cooling, the thus obtained deformation remains constant.

The above-described method provides for especially accurate fitting between the pins and the openings. This method also has the advantage that the pins are inserted into the plate with absolutely identical depths of insertion. The pins do not adhere to the plate, inasmuch as during the thermal treatment in thermostatically adjustable circulating air an overheating of the plate material and the pins and thereby oxidation of the outer surface of the pins do not take place.

The above-mentioned method can be modified in different ways. In accordance with one modification, the plate with the pins after heating is removed from the heating device and all pins are pressed into the plate during additional operational steps. This is performed in a simplified manner when a heavy metallic plate member is placed on the free ends of the pins and the pins are pressed into the plate under the action of the weight of this plate member. The pressing of the pins into the plate can be performed manually, for example with the utilization of a vise.

In accordance with a second modification, the pins during heating are pressed into the openings of the plate by themselves. In this case a pressure arrangement is utilized in which a pressure-transmitting plate member is movable on guiding rods toward a supporting plate member. The pressure-transmitting plate member can be pre-stressed by its own weight or, preferably, with the utilization of a spring element, in direction toward the supporting plate member. The plate with the loosely inserted pins is clamped between the supporting plate member and the pressure-transmitting plate member and introduced into the heating air circulating device. After the respective thermal treatment the pins slide by themselves into the openings. If desired, it is possible to deliver impacts against the above-mentioned pressure device to guarantee that the pins do not completely penetrate through the plate.

In accordance with a third modification, the plate is first heated. Then all pins are inserted into the openings and pressed simultaneously into the plate by placing of the pressure-transmitting plate thereon.

When the pins are pressed into the openings of the plate outside of the heating arrangement, the above-described orientation arrangement for manufacturing of the denture mold can be utilized as the pressing device. A metal frame can be so placed onto the holder that a portion of the metal frame from the lower side abuts against the arms. This portion serves as the pressure-transmitting plate member which is brought into abutment against the free ends of the pins.

The latter described method has the following important advantages. Generally, the pins are introduced into the plate so that their ends abut against the holding plate and are flush with the lower plate face. This position does not change when the plate significantly expands in horizontal and vertical directions because of its heating. However, when the plate assumes its original form after cooling, the pins somewhat extend outwardly beyond the lower face of the plate. By pressing the outwardly extending projections, the pins can easily be pushed out of the plate.

It should finally be emphasized that the present invention provides for faster manufacture of a denture mold than the prior art.

It will be understood that each of the elements described above, or two or more together, may also find a useful application in other types of constructions differing from the types described above.

While the invention has been illustrated and described as embodied in a denture mold as well as a method of and an arrangement for manufacturing of the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A denture mold for making teeth prostheses, such as fillings, crowns, bridges, denture parts and the like, comprising a base element for releasably supporting a positive copy of teeth and made of a mold material; and a plurality of pins arranged to connect the positive copy with said base element, said base element being formed as a prefabricated plate of a shape-retaining material and said pins being arranged on said plate parallel to one another and fixed on the same, so that said plate serves as a holder for said pins during making of the positive copy, whereupon said plate serves as a base of the denture mold, each of said pins being elongated and having at least two portions, as considered in direction of elongation, said portions having different cross-sections separated by a separation plane and a maximum cross-section in said plane, said portions of each of said pins being conical and having base faces superimposed over one another.

2. A denture mold as defined in claim 1, wherein said plate is constituted of a transparent material.

3. A denture mold as defined in claim 2, wherein said plate is constituted of a pellucid material.

4. A denture mold as defined in claim 1, wherein said plate is constituted of a material having a low melting point.

5. A denture mold as defined in claim 1, wherein said plate is constituted of a thermoplastic material.

6. A denture mold as defined in claim 5, wherein said plate is constituted of acrylic glass.

7. A denture mold as defined in claim 1, particularly with the positive copy made in correspondence with a denture impression of at least a portion of at least one of jaws, wherein said plate has a contour corresponding to that of the portion of the one jaw.

8. A denture mold as defined in claim 7, wherein said plate has two guiding surfaces which are parallel to one another and an abutting surface, said guiding surfaces being provided with guiding means.

9. A denture mold as defined in claim 8, wherein said guiding means includes guiding grooves formed in said guiding surfaces of said plate.

10. A denture mold as defined in claim 8, wherein said guiding means includes guiding projections formed on said guiding surfaces of said plate.

11. A denture mold as defined in claim 7, wherein said plate has a polygonal contour.

12. A denture mold as defined in claim 11, wherein said plate has side edges which are substantially parallel to the tangents of the outer surfaces of the last molar teeth, eye-teeth and front teeth.

13. A denture mold as defined in claim 1, wherein said pins are anchored in said plate.

14. A denture mold as defined in claim 13, wherein said pins are releasably anchored in said plate.

15. A denture mold as defined in claim 13, wherein said pins are non-releasably anchored in said plate.

16. A denture mold as defined in claim 1, wherein each of said pins has a portion which is insertable in a respective one of said openings and has a predetermined shape, said openings expanding by a local heating of said plate and having in expanded condition a shape corresponding to the shape of said portion of said pins.

17. A denture mold as defined in claim 1; and further comprising a plurality of mounting members anchored in said openings, said pins being mounted in said mounting members.

18. A denture mold as defined in claim 17, wherein said mounting members are sleeve-shaped.

19. A denture mold as defined in claim 1, wherein said plate has a rear side, said pins somewhat extending outwardly beyond said rear side of said plate.

20. A denture mold as defined in claim 1, wherein said plate contacts said positive copy of mold material over a contact plane, said portions of each of said pins being arranged so that said separation plane and thereby said maximum cross-section coincides with the contact plane.

21. A denture mold as defined in claim 1, wherein at least one of said conical portions of each of said pins has at least one guiding face arranged to prevent rotation of said pins.

22. A denture mold as defined in claim 1, wherein each of said pins is a punched member.

23. A denture mold as defined in claim 1, wherein each of said pins is a stamped member.

24. A denture mold as defined in claim 1, wherein each of said pins is provided with a plurality of depressions.

25. A denture mold as defined in claim 1, wherein each of said pins is provided with a plurality of through openings.

26. A method of manufacturing a denture mold for teeth prostheses, such as fillings, crowns, bridges, denture parts and the like, comprising the steps of forming a negative denture impression; providing a prefabricated plate of a shape-retaining transparent material; arranging a plurality of pins on the plate so that they extend parallel to one another from the latter in correspondence with the negative denture impression, said arranging including bringing the denture impression and the plate to a corresponding position over one another and individually determining fixing points for arranging the pins on the plate, said determining including determining the fixing points by directing a narrowly concentrated light beam through the transparent plate onto the denture impression; filling the negative denture impression with a mold material; dipping the pins into the mold material and hardening the latter to form a positive copy of the teeth, so that during the hardening the plate serves as a holder for all pins, whereas after the hardening the plate serves as a base of the denture mold.

27. A method of manufacturing a denture mold for teeth prostheses, such as fillings, crowns, bridges, denture parts and the like, comprising the steps of forming a negative denture impression; providing a prefabricated plate of a shape-retaining material; arranging a plurality of pins on the plate so that they extend parallel to one another from the latter in correspondence with the negative denture impression, said arranging step including bringing the denture impression and the plate to a corresponding position over one another and individually determining fixing points for arranging the pins on the plate, and also forming a plurality of openings for the pins at the locations of the fixing points in the plate, heating the pins and subsequently pressing the pins directly into the openings; filling the negative denture impression with a mold material; dipping the pins into the mold material and hardening the latter to form a positive copy of the teeth, so that during the hardening the plate serves as a holder for all pins, whereas after the hardening the plate serves as a base of the denture mold.

28. A method of manufacturing a denture mold for teeth prostheses, such as fillings, crowns, bridges, denture parts and the like, comprising the steps of forming a negative denture impression; providing a prefabricated plate of a shape-retaining material; arranging a plurality of pins on the plate so that they extend parallel to one another from the latter in correspondence with the negative denture impression, said arranging including bringing the denture impression and the plate to a corresponding position over one another and individually determining fixing points for arranging the pins on the plate, and also forming a plurality of openings for pins at the locations of the fixing points in the plate, heating the plate in the region of the openings so as to expand the latter, and pressing the pins in cold state directly into the thus expanded openings; filling the negative denture impression with a mold material; dipping the pins into the mold material and hardening the latter to form a positive copy of the teeth, so that during the hardening the plate serves as a holder for all pins, whereas after the hardening the plate serves as a base of the denture mold.

29. A method of manufacturing a denture mold for teeth prostheses, such as fillings, crowns, bridges, denture parts and the like, comprising the steps of forming a negative denture impression; providing a prefabricated plate of a shape-retaining material; arranging a plurality of pins on the plate so that they extend parallel to one another from the latter in correspondence with the negative denture impression, said arranging step including bringing the denture impression and the plate to a corresponding position over one another and individually determining fixing points for arranging the pins on the plate, and also forming a plurality of openings for the pins at the locations of the fixing points in the plate and with a shape differing from that of the pins and plasticizing the material of the plate so as to bring openings to a shape corresponding to that of the pins; filling the negative denture impression with a mold material; dipping the pins into the mold material and hardening the latter to form a positive copy of the teeth, so that during the hardening the plate serves as a holder for all pins, whereas after the hardening the plates serves as a base of the denture mold.

30. A method of manufacturing a denture mold for teeth prostheses, such as fillings, crowns, bridges, denture parts and the like, comprising the steps of forming a negative denture impression; providing a prefabricated plate of a shape-retaining material having a low melting point; arranging a plurality of pins on the plate so that they extend parallel to one another from the latter in correspondence with the negative denture impression, said arranging including heating the pins and pressing the latter in heated state into the plate without preliminarily providing openings in the plate; filling the negative denture impression with a mold material; dipping the pins into the mold material and hardening the latter to form a positive copy of the teeth, so that during the hardening the plate serves as a holder for all pins, whereafter the hardening the plates serves as a base of the denture mold.

31. A method of manufacturing a denture mold for teeth prostheses, such as fillings, crowns, bridges, denture parts and the like, comprising the steps of forming a negative denture impression; providing a prefabricated plate of a shape-retaining material; arranging a plurality of pins on the plate so that they extend parallel to one another from the latter in correspondence with the negative denture impression, said arranging including heating the plate and pressing all pins into the heated plate simultaneously in one working step; filling the negative denture impression with a mold material; dipping the pins into the mold material and hardening the latter to form a positive copy of the teeth, so that during the hardening the plate serves as a holder for all pins, whereas after the hardening the plate serves as a base of the denture mold.

32. A method as defined in claim 31, wherein said arranging step further includes forming a plurality of openings in the plate, inserting the pins into the openings without application of force, heating the pins together with the heating of the plate, said heating step including heating the plate together with the pins inserted therein, and said pressing step including pressing all the pins simultaneously in one step and transmitting to the pins pressure by pressure-transmitting means.

33. A method as defined in claim 32, wherein said transmitting step includes utilizing two parallel plate members as the pressure-transmitting means and holding the plate with the pins between said plate members, said heating step including heating by hot circulating air so that the pins displace by themselves into the openings and deform the latter when the plate in the region of the openings becomes deformable because of the heating.

34. A method as defined in claim 33, wherein said providing step includes utilizing the plate of acrylic glass, and said heating step including heating by hot circulating air to substantially 200° C.

35. A method of manufacturing a denture mold for teeth prostheses, such as fillings, crowns, bridges, denture parts and the like, comprising the steps of forming a negative denture impression; providing a prefabricated plate which is composed of a shape-retaining material so that the plate itself can serve as a base of the denture mold and at the same time does not have pin-receiving openings; placing the plate in an exactly predetermined position relative to the negative denture impressions by bringing the denture impression and the plate to a corresponding position over one another; individually determining on the plate in this position fixing points for arranging pins, in correspondence with the negative denture impression, forming a plurality of openings in the plate at the thus determined fixing points; arranging a plurality of pins on the plate in the thus formed openings and thereby at the thus determined fixing points so that the pins extend parallel to one another from the plate in correspondence with the negative denture impression; and filling the negative denture impression with a mold material in the predetermined position of the plate so that the pins dip in the mold material and after hardening the latter a positive copy of the teeth is formed with the pins dipped therein, whereby during the hardening the plate serves as a holder for all pins, whereas after the hardening the plate serves as a base of the denture mold.

36. A method as defined in claim 35, wherein said determining step includes placing a marking element at a desired location of the denture impression, and providing contact of the plate with the marking element so as to mark the former.

37. A method as defined in claim 36, wherein said placing step includes utilizing a drill as the marking element.

38. A method as defined in claim 36, wherein said placing step includes utilizing a hot needle as the marking element.

39. A method as defined in claim 36, wherein said placing step includes utilizing a soldering bit as the marking element.

40. A method as defined in claim 35, wherein said arranging step includes pressing the pins directly into the openings.

41. A method as defined in claim 35, wherein said arranging step includes anchoring a plurality of sleeves in the plate and mounting the pins on the sleeves.

* * * * *